(12) United States Patent
Alizadeh et al.

(10) Patent No.: US 10,919,018 B2
(45) Date of Patent: Feb. 16, 2021

(54) DEVICE FOR DNA SAMPLE FRAGMENTATION CONFIGURED TO PRODUCE ULTRASONIC WAVES

(71) Applicant: Etablissement Français du Sang, La Plaine Saint Denis (FR)

(72) Inventors: Medhi Alizadeh, Rennes (FR); Cyrus Mahdjoubi, Queven (FR)

(73) Assignee: ETABLISSEMENT FRANAIS DU SANG, La Plaine Saint Denis (FR)

( * ) Notice: Subject to any disclaimer, the term of this patent is extended or adjusted under 35 U.S.C. 154(b) by 0 days.

(21) Appl. No.: 16/094,798

(22) PCT Filed: Jun. 19, 2017

(86) PCT No.: PCT/FR2017/051609
§ 371 (c)(1),
(2) Date: Jan. 28, 2019

(87) PCT Pub. No.: WO2017/182763
PCT Pub. Date: Oct. 26, 2017

(65) Prior Publication Data
US 2019/0143292 A1    May 16, 2019

(51) Int. Cl.
*B01J 19/10*     (2006.01)
*B01F 11/02*     (2006.01)
(Continued)

(52) U.S. Cl.
CPC ......... *B01J 19/10* (2013.01); *B01F 11/0283* (2013.01); *B01L 9/06* (2013.01); *B06B 3/00* (2013.01);
(Continued)

(58) Field of Classification Search
CPC ... B01J 19/10; B01L 9/06; G01N 1/28; C12Q 1/6806; C12Q 2523/301; B06B 3/00; B01F 11/0283; B01F 3/182; B01F 7/00558
See application file for complete search history.

(56) References Cited

U.S. PATENT DOCUMENTS 2,519,657 A * 8/1950 Hunter .................... B01F 13/04
366/305
2,657,668 A * 11/1953 Maier ...................... B01J 19/10
118/612

(Continued)

FOREIGN PATENT DOCUMENTS

CA    2962594 A1 * 3/2016 .......... B01F 11/0283
CH    411414 A  *  4/1966 ............... B06B 3/00

(Continued)

OTHER PUBLICATIONS

International Search Report and Written Opinion for PCT/FR2017/051609 dated Sep. 19, 2017.
French Search Report for FR1653466 dated Dec. 21, 2016.

*Primary Examiner* — Charles Cooley
(74) *Attorney, Agent, or Firm* — Patterson Thuente Pedersen, P.A.

(57) ABSTRACT

A device for the fragmentation of DNA samples. The DNA samples are in solution in a container the device including —a vessel for receiving a liquid, the vessel being configured to produce ultrasonic waves so as to spread ultrasonic waves through the liquid. The device further includes a first support element resting on the vessel, the device further includes a second support element having a passage designed to receive the container. The second support element can be suspended by at least one suspension element forming at least one joint, such that a lower portion of the container can be immersed in the liquid.

10 Claims, 3 Drawing Sheets

(51) Int. Cl.
  *B06B 3/00* (2006.01)
  *C12Q 1/6806* (2018.01)
  *G01N 1/28* (2006.01)
  *B01L 9/06* (2006.01)

(52) U.S. Cl.
  CPC .............. *C12Q 1/6806* (2013.01); *G01N 1/28* (2013.01); *C12Q 2523/301* (2013.01)

(56) References Cited

U.S. PATENT DOCUMENTS

| | | | | |
|---|---|---|---|---|
| 2,932,493 | A | * | 4/1960 | Jacobs ................ B01F 13/0827 366/274 |
| 2,941,908 | A | * | 6/1960 | Logan ..................... B01J 19/10 134/1 |
| 3,285,579 | A | * | 11/1966 | Guerin ................ B01F 11/0208 366/119 |
| 3,331,589 | A | * | 7/1967 | Hammitt ............ B01D 19/0078 366/116 |
| 3,519,251 | A | * | 7/1970 | Nystrom .................. B06B 3/00 366/118 |
| 3,661,660 | A | * | 5/1972 | Wessells .................. B01J 19/10 430/309 |
| 3,955,270 | A | * | 5/1976 | Loya ........................ B01J 19/10 438/465 |
| 9,903,747 | B2 | * | 2/2018 | Rizun .................... G01F 19/005 |
| 2017/0246601 | A1 | * | 8/2017 | Krufka ................ B01F 11/0283 |
| 2019/0143292 | A1 | * | 5/2019 | Alizadeh ............ B01F 11/0283 |

FOREIGN PATENT DOCUMENTS

| | | | | |
|---|---|---|---|---|
| CH | 457000 | A | * 5/1968 | .............. B01J 19/10 |
| DE | 910849 | C | * 5/1954 | .............. B01J 19/10 |
| DE | 959990 | C | * 3/1957 | ............ B01F 3/1242 |
| EP | 2511380 | | 10/2012 | |
| FR | 1381821 | A | * 12/1964 | ............ B01F 3/0407 |
| FR | 1541739 | A | * 10/1968 | .............. B01F 11/02 |
| FR | 3050211 | A1 | * 10/2017 | .......... B01F 11/0283 |
| GB | 1240592 | A | * 7/1971 | .......... B01F 11/0025 |
| JP | 57028182 | A | * 2/1982 | .......... B01F 11/0283 |

* cited by examiner

DEVICE FOR DNA SAMPLE FRAGMENTATION CONFIGURED TO PRODUCE ULTRASONIC WAVES

RELATED APPLICATIONS

The present application is a National Phase entry of PCT Application No. PCT/FR2017/051609, filed Jun. 19, 2017, which claims priority to FR 1653466, filed Apr. 19, 2016, the contents of each being incorporated herein by reference in their entireties.

TECHNICAL FIELD

The invention relates to the field of DNA fragmentation which consists in obtaining, from a strand of DNA comprising a large number of nucleotide bases, several portions of a strand comprising a more restricted number of nucleotide bases. The invention more particularly relates to a device for the fragmentation of DNA samples.

BACKGROUND ART

Devices are known for the fragmentation of DNA samples, the samples being in solution in a dedicated container. Such devices conventionally comprise a vessel for receiving a liquid, the vessel being provided with means for producing ultrasonic waves so as to spread ultrasonic waves through the liquid; and a support element resting on the vessel designed to receive the container. The means for producing ultrasonic waves is designed to generate a field of ultrasonic waves with predefined properties in a limited space of the vessel. This characteristic limits the number of DNA samples that it is possible to simultaneously fragment in the device. A fragmentation process lasts on the average one minute. Currently, the maximum number of fragmented samples simultaneously by such a device is about eight. However, the samples are conventionally stored in plates comprising a hundred wells in order to be able to contain a hundred samples. In a perspective of productivity, it would be interesting to simultaneously fragment all of the samples of a plate.

Furthermore, the devices for the fragmentation of DNA samples often impose the use of specific containers, in particular when the container plays a role in the production or the transmission of ultrasonic waves. This imposes a transfer of the samples from an initial container to a specific container, which constitutes a time-consuming manipulation. Moreover, these specific containers represent an additional cost for the user.

SUMMARY

Embodiments of the invention propose a solution aiming to overcome the aforementioned disadvantages while guaranteeing a device that performs at least as well as what exists with a limited production cost, in particular the duration of the fragmentation process is maintained at about one minute and the homogeneity of the length of the DNA strands obtained following the fragmentation is equivalent to what exists. Embodiments of the invention propose a solution that solves the technical problem of the creating of a substantially homogenous ultrasonic field in a volume that contains a large number of DNA samples without using a specific container. An objective of embodiments of the invention is to allow for the use of standard containers in the device for the fragmentation of DNA samples and in particular the use of plates able to contain a hundred samples, and even more, for the purpose of increasing the productivity of such a device.

Embodiments of the invention relate to a device for the fragmentation of DNA samples that are in solution in a container, the device comprising a vessel for receiving a liquid, the vessel being provided with means for producing ultrasonic waves so as to spread ultrasonic waves through the liquid; and a first support element resting on the vessel, the device being characterized in that it further comprises a second support element comprising a passage designed to receive the container, the second support element being suspended from at least one suspension element at a certain distance from said the first support element by at least one suspension element forming at least one swivel joint in such a way as to allow for the immersion of a lower portion of the container in the liquid. The term swivel joint means a connection that entirely connects two parts in translation but leaves them free in rotation. Such a connection therefore comprises 3 degrees of connections in translation and 3 degrees of freedom in rotation. The suspension element forming a swivel joint makes it possible to substantially attenuate the transmission of interfering ultrasonic waves from the first support element to the second support element thanks to a damping effect of the swivel joint. More generally, the device is designed to inhibit as much as possible the transmission of interfering ultrasonic waves to the container. Eliminating interfering ultrasonic waves contributes to creating a field of ultrasonic waves that is substantially homogeneous in the vicinity of the container. Furthermore, the container is not imposed by the device and varied shapes of the container are suitable. According to an advantageous embodiment, the container is a plate comprising a plurality of wells. Preferably, this plate is a standard plate commonly used to transport and/or treat DNA samples.

According to a particular embodiment, the suspension element is deformable in order to limit the propagation of the interfering waves between the first support element and the second support element.

According to a particular embodiment, the suspension element comprises a means for adjusting arranged to modify the distance between the first support element and the second support element. The means for adjusting make it possible to adjust the horizontality of the second support element and therefore of the container and to adjust the position of the second support element with respect to the bottom of the vessel and therefore the position of the container with respect to the liquid.

According to a particular embodiment, the means for producing ultrasonic waves comprises at least one ultrasonic transducer transforming an electrical signal into a mechanical signal. Preferably, the means for producing ultrasonic waves comprise a plurality of transducers arranged according to a grid so as to create a relatively homogeneous field of ultrasonic waves in the vicinity of the container.

According to a particular embodiment, the means for producing ultrasonic waves further comprises a signal generator arranged to supply the transducer with an electric signal.

According to a particular embodiment, the signal generator comprises a module for generating periodic signals. For example, the signal generator comprises at least one piezoelectric oscillator.

According to a particular embodiment, the signal generator further comprises a signal amplifier that makes it possible to amplify the signal generated by the module for generating periodic signals before transmitting the signal to the transducer.

According to a particular embodiment, the signal generator further comprises a frequency and/or phase scanning module in such a way as to generate at least two signals having separate frequencies and/or phases in a predetermined frequency band. The frequency and/or phase scanning makes it possible to prevent the appearance of fixed antinodes and nodes in stationary operation in the presence of periodic waves.

According to a particular embodiment, the means for producing ultrasonic waves is fastened onto an outer lower face of the vessel. For example, the transducers are glued onto the bottom of the vessel by means of an adhesive suitable for the transmission of ultrasonic waves or are welded to the vessel. The means for producing ultrasonic waves transmits the ultrasonic waves to the lower face of the vessel, then the lower face of the vessel transmits in turn the ultrasonic waves to the liquid.

According to a particular embodiment, when the device is in operating position, the means for producing ultrasonic waves is placed substantially vertically with the passage of the second support element in such a way as to be centered with respect to the passage. The vertical is defined as being the direction of the force of gravity. The presence of the means for producing ultrasonic waves at the vertical of the passage of the second support element and therefore at the vertical of the container contributes to creating a homogeneous field of ultrasonic waves in the vicinity of the container via a symmetrical effect. However, the symmetry is optional.

According to a particular embodiment, the device comprises a second means for producing ultrasonic waves in order to actively reduce, and even cancel, the interfering ultrasonic waves.

According to a particular embodiment, the first support element comprises a passage in such a way as to allow a user to access the passage of the second support element. The access to the passage of the second support element makes it possible to place a container in the second support element or to withdraw it therefrom.

According to a particular embodiment, the suspension element comprises at least three chains in swivel joint with the upper plate and in swivel joint with the support. The three chains are distributed in such a way as to make it possible to maintain the second support element in a horizontal position while still guaranteeing the degrees of mobility of a swivel joint. The horizontality is defined as being perpendicular to the vertical direction.

According to a particular embodiment, the second support element is separate from the lateral faces of the vessel by a predetermined distance, for example a distance of 10 centimeters, in such a way as to limit the exposure of the container to the edge effects in the vicinity of the lateral faces created by the reflection of the ultrasonic waves by the lateral faces. This characteristic contributes to the homogeneity of the field of ultrasonic waves in the vicinity of the container.

According to a particular embodiment, the device further comprises an outer frame wherein the vessel is placed. The frame makes it possible to support the vessel and to isolate the outer environments from the ultrasonic waves propagating in the vessel.

According to a particular embodiment, the device comprises a cover. The cover makes it possible to isolate the contents of the vessel from the outside environment with a concern for safety and hygiene.

According to a particular embodiment, the device further comprises an overflow device intended to ensure the presence of a predetermined level of liquid in the vessel. It is necessary that the level of liquid by sufficiently high to immerse the portion of the container comprising the DNA samples to be fragmented. However, it is preferable that the second support element not be immersed in order to prevent the edge effects linked to the reflection of the ultrasonic waves on the second support element, which would be detrimental to the homogeneity of the field of ultrasonic waves.

According to a particular embodiment, the overflow device comprises a drainage passage so as to remove an excess portion of the liquid.

According to a particular embodiment, the device further comprises a means for adjusting the horizontality of the vessel in order to guarantee a homogeneous immersion of all of the wells of the container in the liquid.

According to a particular embodiment, the means for adjusting the horizontality of the vessel comprises adjustable legs.

According to a particular embodiment, the means for adjusting the horizontality of the vessel comprises a bubble spirit level.

BRIEF DESCRIPTION OF THE DRAWINGS

Other innovative characteristics and advantages shall appear in the description hereinafter, provided for the purposes of information and in no way limiting, in reference to the accompany drawings, wherein.

DETAILED DESCRIPTION

Figure 1A:
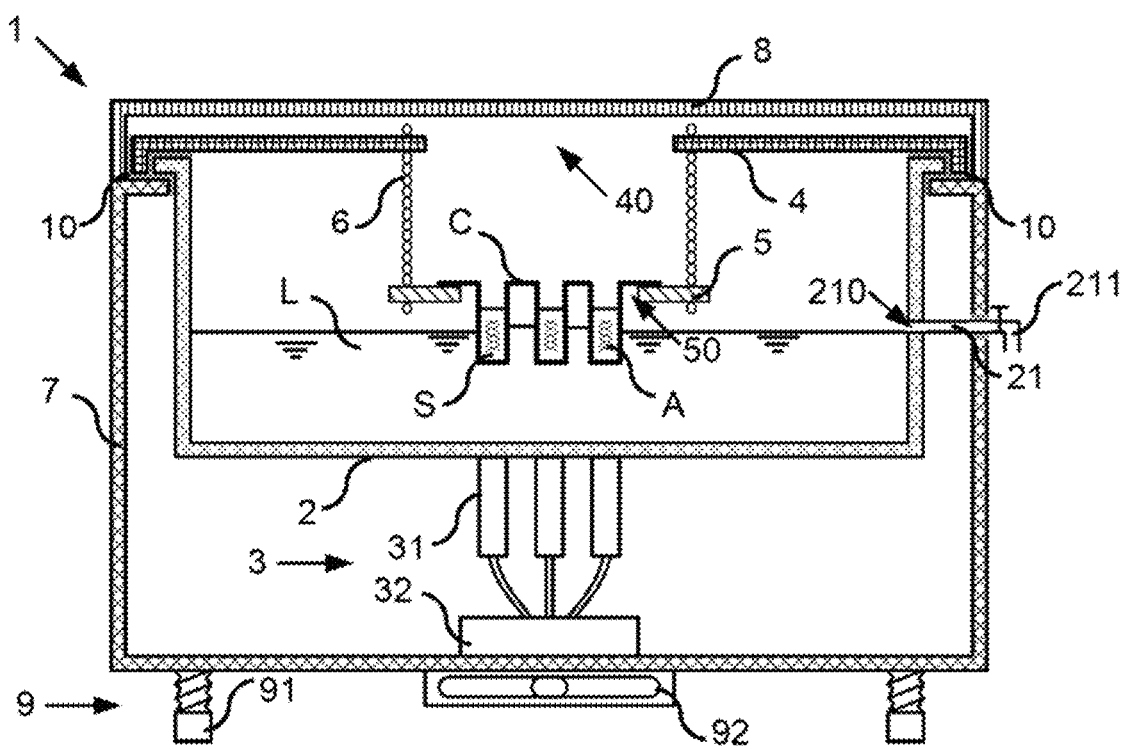
FIGS. 1a and 1b show a diagrammatical view and as a cross-section of a device respectively according to a first and a second embodiment of the invention.
Figure 1B:
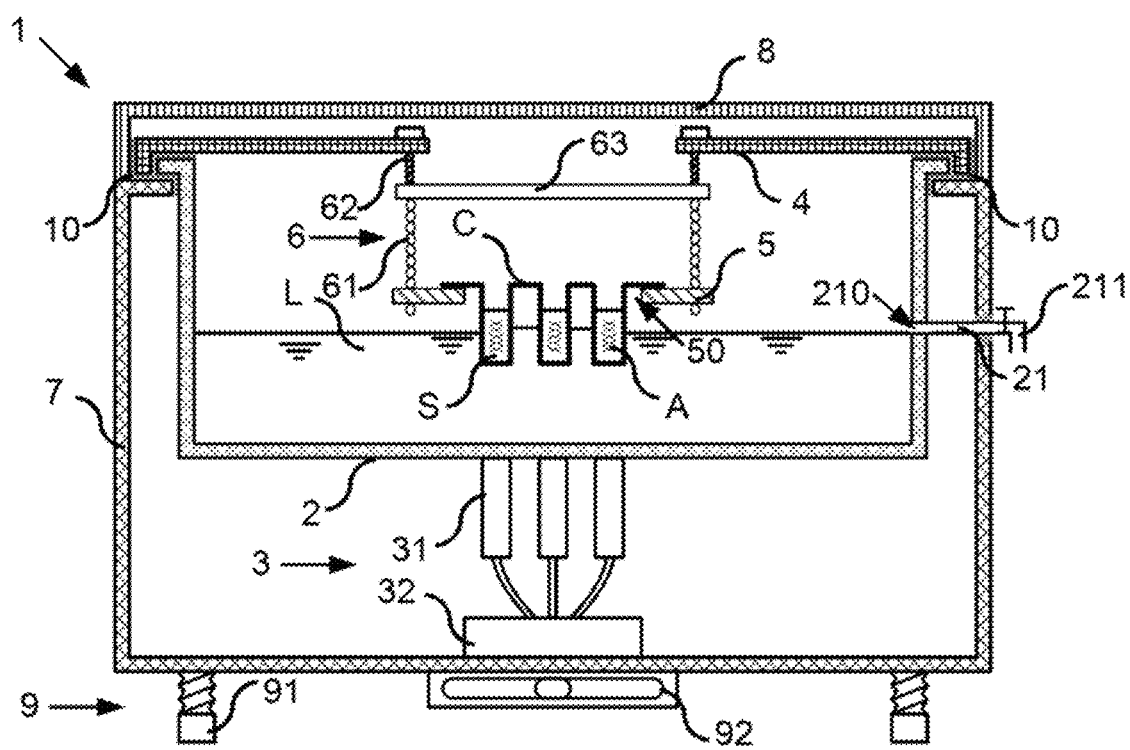
Figure 2:
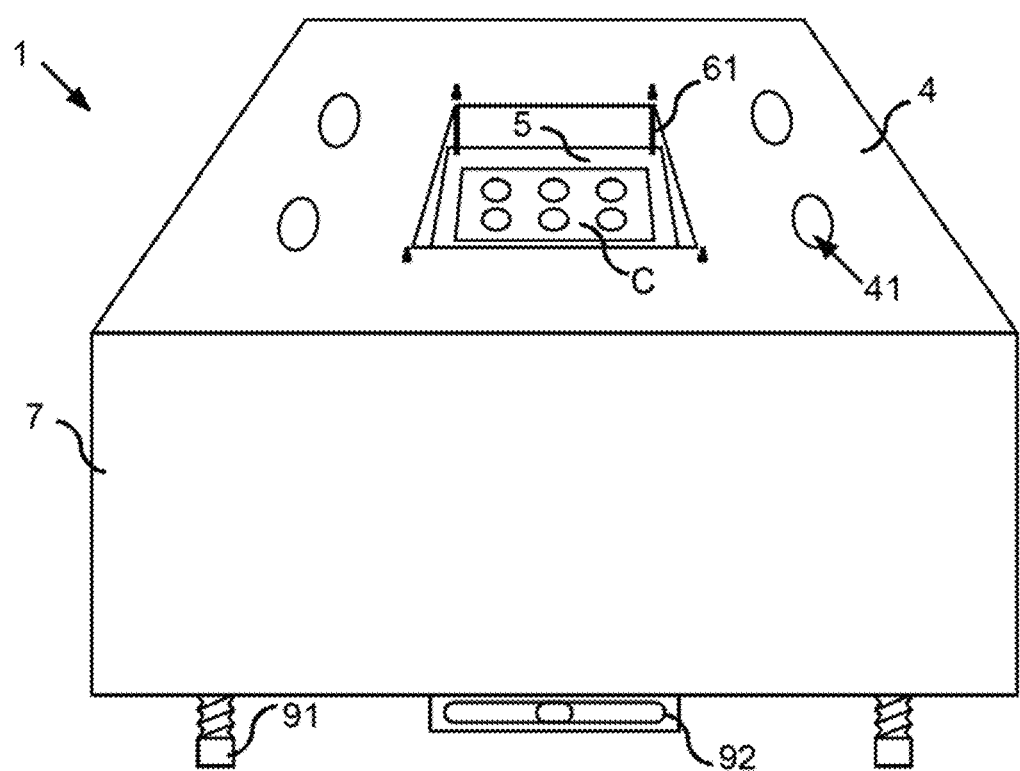
FIG. 2 shows a diagrammatical view in perspective of the device of FIG. 1a or of FIG. 1b.

FIGS. 1a, 1b and 2 show a device 1 for the fragmentation of DNA samples. The DNA samples to be fragmented are placed in solution in a solution S and placed in a container C. For example, the fragmentation device 1 makes it possible to obtain from a genome comprising substantially 3 billion nucleotide bases, several strand portions comprising substantially 400 bases. The solution S used is typically water or an aqueous gel. The container C is preferably a standard container, for example a plate comprising a plurality of wells arranged according to a grid pattern, or a row of test tubes.

The device 1 comprises a vessel 2, a means for producing ultrasonic waves 3, a first support element 4, a second support element 5, a suspension element 6, a frame 7, a cover 8 and a means for adjusting the horizontality 9 of the vessel.

The vessel 2 is a sealed container designed to receive a liquid L, typically water. The vessel 2 is advantageously made of metal and more particularly of stainless steel so as to prevent the oxidation of the vessel 2 in contact with water and to facilitate the cleaning thereof with a concern for hygiene. The vessel 2 has for example a parallelepiped shape and comprises a lower face and four lateral faces. From a dimensional standpoint and purely for the purposes of illustration, the lower face is substantially of rectangular shape and its sides measure between 25 and 35 centimeters. The lateral faces have a vertical dimension of about ten centimeters, with the vertical being defined by the direction of the force of gravity.

The vessel 2 is placed in the frame 7. The frame is a container able to insulate the outside environment from the ultrasonic waves propagating in the vessel 2. The frame 7 is advantageously made of metal and more particularly of stainless steel. The frame 7 has for example a parallelepiped shape and comprises a lower face and four lateral faces. From a dimensional standpoint and purely for the purposes of illustration, the lower face is substantially of rectangular shape and its sides measure about forty centimeters. The lateral faces have a vertical dimension of about twenty centimeters.

The lateral faces of the vessel 2 comprise upper edges resting on the lateral faces of the frame 7 in such a way that a space is present between the outer lower face of the vessel 2 and the inner lower face of the frame 7. Advantageously, the interfaces between the upper edges of the vessel 2 and the lateral faces of the frame 7 comprise joints 10 that limit the propagation of interfering waves between the vessel 2 and the frame 7.

The first support element 4 has for example substantially the shape of a plate comprising edges. From a dimensional standpoint and purely for the purposes of illustration, the plate is substantially of rectangular shape and its sides measure between 25 and 35 centimeters. The first support element 4 is removably nested on the edges of the lateral faces of the vessel in such a way as to guarantee a substantially fixed position of the first support element 4 in relation to the vessel 2. Advantageously, the nesting of the first support element 4 with the vessel has a clearance for example filled with damping joints 10 that limit the propagation of interfering waves between the vessel 2 and the first support element 4. The first support element 4 comprises a passage 40 substantially at its center. From a dimensional standpoint and purely for the purposes of illustration, the passage 40 is substantially of rectangular shape and its sides measure about fifteen centimeters. The first support element 4 is advantageously made of metal and more particularly of stainless steel so as to prevent the oxidation thereof in contact with water and to facilitate the cleaning thereof. The first support element 4 comprises advantageously handles 41 that facilitate the handling thereof. For example, the handles 41 are sets of two passages in the first support element arranged to make it possible to grasp the first support element by respectively inserting two fingers into the passages in such a way as to pinch the first support element 4.

The second support element 5 has substantially for example a plate shape. From a dimensional standpoint and purely for the purposes of illustration, the plate is substantially of rectangular shape and its sides measure about fifteen centimeters. The second support element 5 comprises a passage 50 substantially at its center. From a dimensional standpoint and purely for the purposes of illustration, the passage 50 is substantially of rectangular shape and its sides measure about ten centimeters. The second support element 5 is advantageously made of metal and more particularly of stainless steel so as to prevent the oxidation thereof in contact with water and to facilitate the cleaning thereof.

The second support element 5 is suspended from the first support element 4 by the suspension element 6 forming a swivel joint. The suspension element 6 advantageously comprises 4 chains 61 respectively connecting four points of the support element 4, in the vicinity of the four corners of the passage 40, to four points of the support element 5, in the vicinity of the four corners of the support 5. Each chain 61 comprises two ends, the first end being as a swivel joint with the first support element 4 and the second end being as a swivel joint with the second support element 5. According to other embodiments, the chains 61 are replaced with rods, rings or cords. Such suspension elements 6 that can be deformed extend between the first support element 4 and the second support element 5 according to a length for example of about 4 centimeters and make it possible to maintain the second support element substantially at the center of the vessel in horizontal position, the horizontal being defined as being perpendicular to the vertical, while still limiting the transmission of ultrasonic waves through the suspension element 6 thanks to the damping nature conferred by the swivel joint.

According to a particular embodiment shown in FIG. 1*b*, the suspension element 6 comprises a means for adjusting arranged to modify the distance between the first support element 4 and the second support element 5. The means for adjusting comprise two cross members 63 substantially perpendicular to the chains 61 and four screws 62 connecting the first support element 4 to the cross members 63. By screwing or unscrewing the screws 62, the distance between the first support element 4 and the cross members 63 is modified. Advantageously, the four screws 62 are inserted into the first support element 4 respectively at four points of the support element 4 in the vicinity of the four corners of the passage 40. Two adjacent screws are respectively screwed in the two ends of a first cross member, the other screws are respectively screwed in the two ends of the second cross member. Four corners of the second support element 5 in the vicinity of the four corners of the support element 5 are respectively connected to the four ends of the two cross members by chains 61 substantially in the extension of the screws 62.

The second support element 5 is intended to receive a container C, typically a plate comprising a plurality of wells to receive DNA samples. The container C is placed in such a way that the wells are in the passage 50 and that the direction according to which the wells extend is vertical, with the ends of the container, at the periphery of the wells, resting on the second support element 5.

The second support element 5 is separate from the lateral faces of the vessel by a predetermined distance, for example a distance of 10 centimeters, in such a way as to limit the exposure of the container C to the edge effects in the vicinity of the lateral faces created by the reflection of the ultrasonic waves by the lateral faces.

The vessel 2 is filled with liquid L so as to immerse the distal end of the wells and to leave the second support element 5 in the open air so as to prevent the reflection of the ultrasonic waves propagating in the liquid L by the support element 5. The vessel 2 comprises for example between 5 and 7 centimeters of liquid L. During the filling operation of the vessel 2, the first and the second support elements are removed from the vessel 2 in such a way as to pour the liquid L into the vessel 2. The level of liquid L is predefined and must be accurate to the nearest millimeter. In order to precisely control the level of liquid L in the vessel 2, the vessel 2 comprises an overflow device 21. According to the embodiment shown, the overflow mechanism comprises a drainage passage 210 in a lateral face of the vessel at a height corresponding to the desired level of liquid. The excess liquid is removed by a conduit 211. The conduit 211 conveys the excess liquid to the outside of the frame 7 through a passage in the frame 7. According to an embodiment not shown, the excess liquid is collected in a container fastened to the frame 7. According to another embodiment not shown, the overflow device 21 comprises a wall that delimits a sealed compartment in the vessel 2, the wall being arranged so that the excess liquid passes over an upper edge of the wall.

The cover 8 covers the frame 7 and makes it possible to isolate the contents of the vessel 2 from the outside environment with a concern for safety and hygiene. Advantageously, the cover 8 comprises joints 10 at the interfaces between the cover 8 and the first support element 4 or between the cover 8 and the vessel 2 in such a way as to limit the propagation of the interfering waves on these interfaces.

The means for adjusting the horizontality 9 of the vessel comprises adjustable legs 91 and a bubble spirit level 92. In the embodiment shown, the adjustable legs 91 and the bubble spirit level 92 are fastened onto the outer lower face of the frame 7.

The means for producing ultrasonic waves 3 comprises a plurality of transducers 31, for example 6 transducers arranged according to a grid comprising 2 lines of 3 transducers in order to create a relatively homogeneous field of ultrasonic waves in the vicinity of the container C. The transducers transform an electric signal into a mechanical signal generating ultrasonic waves. The transducers are fixed to an outer face of the vessel 2, for example they are glued by means of an adhesive suitable for the transmission of ultrasonic waves or they are welded. Advantageously, the transducers are fastened onto an outer lower face of the vessel, vertical with the passage 50 of the second support element 5.

Figure 3:
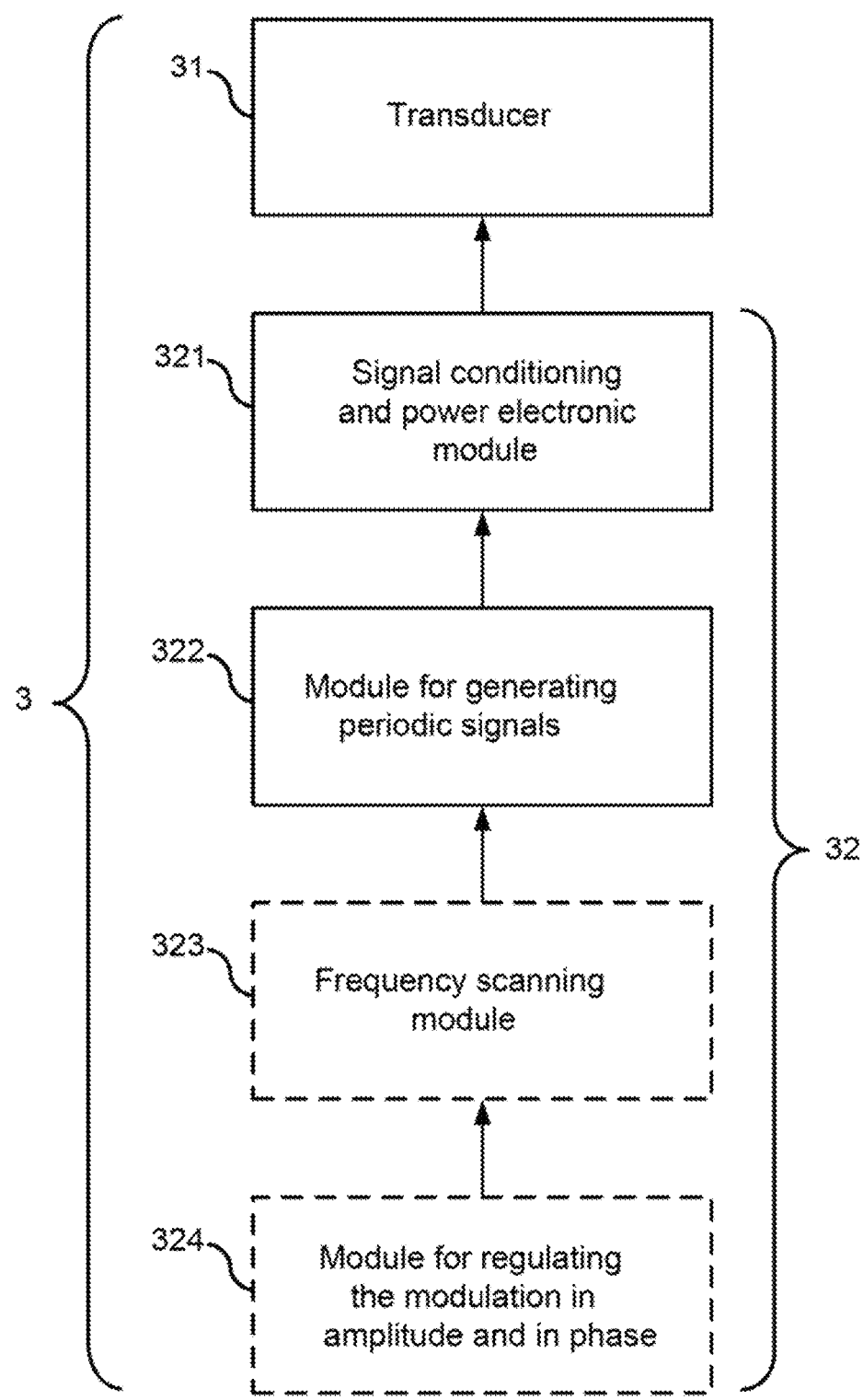
FIG. 3 shows a functional diagram of a means for producing ultrasonic waves according to embodiments of the invention.

FIG. 3 shows a means for producing ultrasonic waves 3. The transducers 31 are supplied with an electrical signal by a signal generator 32. Advantageously, the signal generator 32 comprises a module for generating periodic signals 322, for example a piezoelectric oscillator, and a signal conditioning and power electronic module 321 that amplifies the signal generated by the module for generating periodic signals 322. Advantageously, in order to create a substantially homogenous field of ultrasonic waves in the vicinity of the container and, in particular, so as to prevent the appearance of antinodes and nodes in stationary operation, the signal generator 32 comprises a frequency scanning module 323 in such a way as to generate at least two signals having separate frequencies in a predetermined frequency band, for example a frequency band between 24 kHz and 28 kHz. Advantageously, the signal generator 32 further comprises a module for regulating the modulation in amplitude and in phase so as to be able to vary the amplitude and the phase of the signals generated still with the objective of preventing the appearance of antinodes and nodes.

Embodiments of the invention are described hereinabove as examples. It is understood that those skilled in the art are able to carry out different alternative embodiments of the invention, by associating for example the various characteristics hereinabove taken independently or in combination, without however leaving the scope of the invention.

The invention claimed is:

1. A device for the fragmentation of DNA samples that are in solution in a container by presenting a substantially homogenous field of ultrasonic waves in the vicinity of the container, the device comprising:

a vessel for receiving a liquid, the vessel presenting a lateral face and being provided with means for producing ultrasonic waves so as to spread ultrasonic waves through the liquid;

an outer frame at least partially disposed around at least a portion of the vessel so as to insulate ultrasonic waves propagating within the vessel from an outside environment; and a first support element resting on the vessel, the device further comprising a second support element comprising a passage designed to receive the container, the second support element being suspended from the first support element at a distance from said first support element by at least one suspension element forming at least one joint operably coupling the first support element and the second support element in three degrees of freedom to allow for the immersion of a lower portion of the container in the liquid, the vessel including structure defining an overflow device positioned along the lateral face of the vessel for precisely controlling the level of liquid received by the vessel, whereby the distance that the second support element is suspended from the first support element and the position of the overflow device along the lateral face of the vessel, provide for precise positioning of the container with respect to the level of liquid received by the vessel;

wherein the overflow device includes a conduit extending between the vessel and the outer frame and to an exterior portion of the outer frame so as to convey excess liquid outside of the outer frame.

2. The device according to claim 1 wherein the at least one suspension element is deformable.

3. The device according to claim 1 wherein the at least one suspension element comprises a means for adjusting arranged to modify the distance between the first support element and the second support element.

4. The device according to claim 1 wherein the means for producing ultrasonic waves comprises at least one ultrasonic transducer.

5. The device according to claim 4 wherein the means for producing ultrasonic waves further comprises a signal generator arranged to supply the at least one ultrasonic transducer with an electric signal.

6. The device according to claim 5 wherein the signal generator comprises a module for generating periodic signals.

7. The device according to claim 1 wherein the means for producing ultrasonic waves is fastened onto an outer lower face of the vessel.

8. The device according to claim 7 wherein the means for producing ultrasonic waves is placed substantially vertically with the passage of the second support element.

9. The device according to claim 1 wherein the first support element comprises a passage in such a way as to allow a user to access the passage of the second support element.

10. The device according to claim 1 wherein the second support element is separated from the lateral face of the vessel by a predetermined distance in such a way as to limit the exposure of the container to edge effects in the vicinity of the lateral face created by the reflection of the ultrasonic waves by the lateral face.

* * * * *

UNITED STATES PATENT AND TRADEMARK OFFICE
CERTIFICATE OF CORRECTION

| | | |
|---|---|---|
| PATENT NO. | : 10,919,018 B2 | Page 1 of 1 |
| APPLICATION NO. | : 16/094798 | |
| DATED | : February 16, 2021 | |
| INVENTOR(S) | : Alizadeh et al. | |

It is certified that error appears in the above-identified patent and that said Letters Patent is hereby corrected as shown below:

On the Title Page

Item [73], delete "ETABLISSEMENT FRANAIS DU SANG" and insert -- Etablissement Français du Sang --

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*